(12) United States Patent
Wang et al.

(10) Patent No.: US 7,557,265 B2
(45) Date of Patent: Jul. 7, 2009

(54) PLANT PHYTASE GENES AND METHODS OF USE

(75) Inventors: Zeng-Yu Wang, Ardmore, OK (US);
Maria Harrison, Ardmore, OK (US);
Kai Xiao, Hebei Province (CN)

(73) Assignee: The Samuel Roberts Noble Foundation, Adrmore, OK (US)

( * ) Notice: Subject to any disclaimer, the term of this patent is extended or adjusted under 35 U.S.C. 154(b) by 193 days.

(21) Appl. No.: 11/400,050

(22) Filed: Apr. 7, 2006

(65) Prior Publication Data

US 2006/0253920 A1 Nov. 9, 2006

Related U.S. Application Data

(60) Provisional application No. 60/669,318, filed on Apr. 7, 2005.

(51) Int. Cl.
*A01H 5/00* (2006.01)
*C07H 21/04* (2006.01)
*C12N 15/63* (2006.01)
*C12N 5/14* (2006.01)
*C12N 15/82* (2006.01)

(52) U.S. Cl. ............... 800/295; 536/23.6; 435/320.1; 435/419; 435/468; 800/278; 800/312

(58) Field of Classification Search .................. None
See application file for complete search history.

(56) References Cited

U.S. PATENT DOCUMENTS 6,303,766 B1 10/2001 Grabau et al. ............... 536/23.1
2004/0034888 A1* 2/2004 Liu et al. ..................... 800/289

FOREIGN PATENT DOCUMENTS

WO WO 98/05785 2/1998
WO WO 01/83763 11/2001

OTHER PUBLICATIONS

Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Wells (Biochemistry 29:8509-8517, 1990).*
Abelson, "A potential phosphate crisis," *Science*, 283:2015, 1999.
Brinch-Pederson et al., "Engineering crop plants: getting a handle on phosphate," *Trends in Plant Sci*, 7:118-25, 2002.
Chiou et al., "The spatial expression patterns of a phosphate transporter (MtPT1) from *Medicago truncatula* indicate a role in phosphate transport at the root/soil interface," *The Plant Journal*, 25:281-293, 2001.
Gaston et al., "Phosphorus runoff relationships for Louisiana Coastal Plain soils amended with poultry litter," *J. Environ. Qual.*, 32:1422-1429, 2003.

Hammond et al., "Changes in gene expression in *Arabidopsis* shoots during phosphate starvation and the potential for developing smart plants," *Plant Physiol.*, 132:578-596, 2003.
Hayes et al., "Phytase and acid phosphate activities in extracts from roots of temperate pasture grass and legume seedlings," *J. Plant Physiol.*, 26:801-809, 1999.
Hayes et al., "The growth and phosphorus utilisation of plants in sterile media when supplied with inositol hexaphosphate, glucose 1-phosphate or inorganic phosphate," *Plant and Soil*, 220:165-174, 2000.
Hegeman and Grabau, "A novel phytase with sequence similarity to purple acid phosphatases is expressed in cotyledons of germinating soybean seedlings," *Plant Physiol.*, 126:1598-1608, 2001.
Hübel and Beck, "Maize Root Phytase (Purification, Characterization, and Localization of Enzyme Activity and Its Putative Substrate)," *Plant Physiol.*, 112:1429-1436, 1996.
Li et al., "Secretion of active recombinant phytase from soybean cell-suspension cultures," *Plant Physiol.*, 114:1103-111, 1997.
Liu et al., "Cloning and characterization of two phosphate transporters from *Medicago truncatula* roots: regulation in response to phosphate and to colonization by arbuscular mycorrhizal (AM) fungi," *Molecular Plant Microbe Interactions*, 11:14-22, 1998.
Maugenest et al., Structure of two maize phytase genes and their spatio-temporal expression during seedling development, *Plant Mol. Biol.*, 39:503-514, 1999.
Mudge et al., "Root-specific and phosphate-regulated expression of phytase under the control of a phosphate transporter promoter enables *Arabidopsis* to grow on phytate as a sole P source," *Plant Sci.*, 165:871-878, 2003.
Mukatira et al., "Negative regulation of phosphate starvation-induced genes," *Plant Physiol*, 127:1854-1862, 2001.
Pote et al., "Water-quality effects of incorporating poultry litter into perennial grassland soils.," *J. Environ. Qual.*, 32:2392-2398, 2003.
Potenza et al., "Invited review: targeting transgene expression in research, agricultural, and environmental applications: promoters used in plant transformation," *In Vitro Cellular and Developmental Biology Plant*, 40:1-22, 2004.
Raghothama, "Phosphate acquisition," *Annu. Rev. Plant Physiol. Plant Mol. Biol.*, 50:665-693, 1999.
Richardson et al., "Acid phosphomonoesterase and phytase activities of wheat (*Triticum aestivum* L.) roots and utilization of organic phosphorus by seedlings grown in sterile culture," *Plant Cell Environ.*, 23:397-405, 2000.

(Continued)

*Primary Examiner*—Phuong T Bui
*Assistant Examiner*—Vinod Kumar
(74) *Attorney, Agent, or Firm*—Sonnenschein Nath & Rosenthal LLP

(57) ABSTRACT

The invention provides secreted plant phytase coding sequences. Also provided are constructs comprising these sequences, plants transformed therewith and methods of use thereof. In certain aspects of the invention, transgenic plants are provided exhibiting improved phosphorous utilization. Additionally, the invention provides methods for increasing phosphorous utilization in plants and bioremediation of phosphorous in soil and water.

22 Claims, 7 Drawing Sheets

OTHER PUBLICATIONS

Richardson et al., "Extracellular secretion of *Aspergillus* phytase from *Arabidopsis* roots enables plants to obtain phosphorus from phytate," *Plant J.*, 25:641-649, 2001.

Roe and Kupfer, "Sequencing gene rich regions of *Medicago runcatula*, a model legume," In Molecular Breeding of Forage and Turf, Hopkins et al., (Eds.), Kluwer Academic Publishers, Dordrecht, 333-344, 2004.

Rubio et al., "A conserved MYB transcription factor involved in phosphate starvation signaling both in vascular plants and in unicellular algae," *Genes and Development*, 15:2122-2133, 2001.

Schunamann et al., "Characterization of promoter expression patterns derived from Pht1 phosphate transporter genes of barley (*Hordeum vulgare* L.)," *J. Exp. Botany*, 55:855-865, 2004.

Schunmann et al., "Promoter analysis of the barley Pht1;1 phosphate transporter G root expression and responsiveness to phosphate deprivation," *Plant Physiology*, 136:4205-4214, 2004.

Vance et al., "Phosphorus acquisition and use: critical adaptations by plants for securing a nonrenewable resource," *New Phytol.*, 157:423-447, 2003.

Vohra and Satyanarayana, "Phytases: microbial sources, production, purification, and potential biotechnological applications," *Crit. Rev. Biotechnol.*, 23:29-60, 2003.

Whitelaw, "Growth promotion of plants inoculated with phosphate-solubilizing fungi,"*Advances in Agronomy*, 69:99-151, 2000.

Xiao et al., "Isolation and characterization of root-specific phosphate transporter promoters from *Medicago truncatula*," *Plant Biol*, 8:1-11, 2006.

Xiao et al., "Improved phosphorus acquisition and biomass production in *Arabidopsis* by transgenic expression of a purple acid phosphatase gene *M. truncatula*," *Plant Science*, 170:191-202, 2006.

Xiao et al., "Transgenic expression of a novel *M. truncatula* phytase gene results in improved acquisition of organic phosphorus by *Arabidopsis*," *Planta*, 22:27-36, 2005.

Zimmermann et al. "Engineering the root-soil interface via targeted expression of a synthetic phytase gene in trichoblasts," *Plant Biotechnol. J.*, 1:353-360, 2003.

Charles et al., "Metabolic Activity of the Resting Seeds of *Cuscuta campestris* & Its Host Alfalfa," *Ind. J. Biochem. Biophys.*, 19:106-110, 1982.

Database EMBL Online, "*Arabidopsis thaliana* putative purple acid phosphatase )PAP23) mRNA, complete cds," Database Accession No. AY390530, 2003.

Database EMBL Online, "EST639270 MTUS *Medicago truncatula* cDNA clone MTUS-41G1, mRNA sequence," Database Accession No. CA921552, 2002.

Novak and Chan, "Development of P-Hyperaccumulator Plant Strategies to Remediate Soils with Excess P Concentrations," *Crit. Rev. Plant Sci.*, 21:493-509, 2002.

Ullah et al., "Cloned and Expressed Fungal phyA Gene in Alfalfa Produces a Stable Phytase," *Biochem. Biophys. Res. Commun.*, 290:1343-1348, 2002.

Xiao et al., "Ectopic Expression of a Phytase Gene from *Medicago truncatula* Barrel Medic Enhances Phosphorus Absorption in Plants," *J. Integrative Plant Biol.*, 48:35-43, 2006.

\* cited by examiner

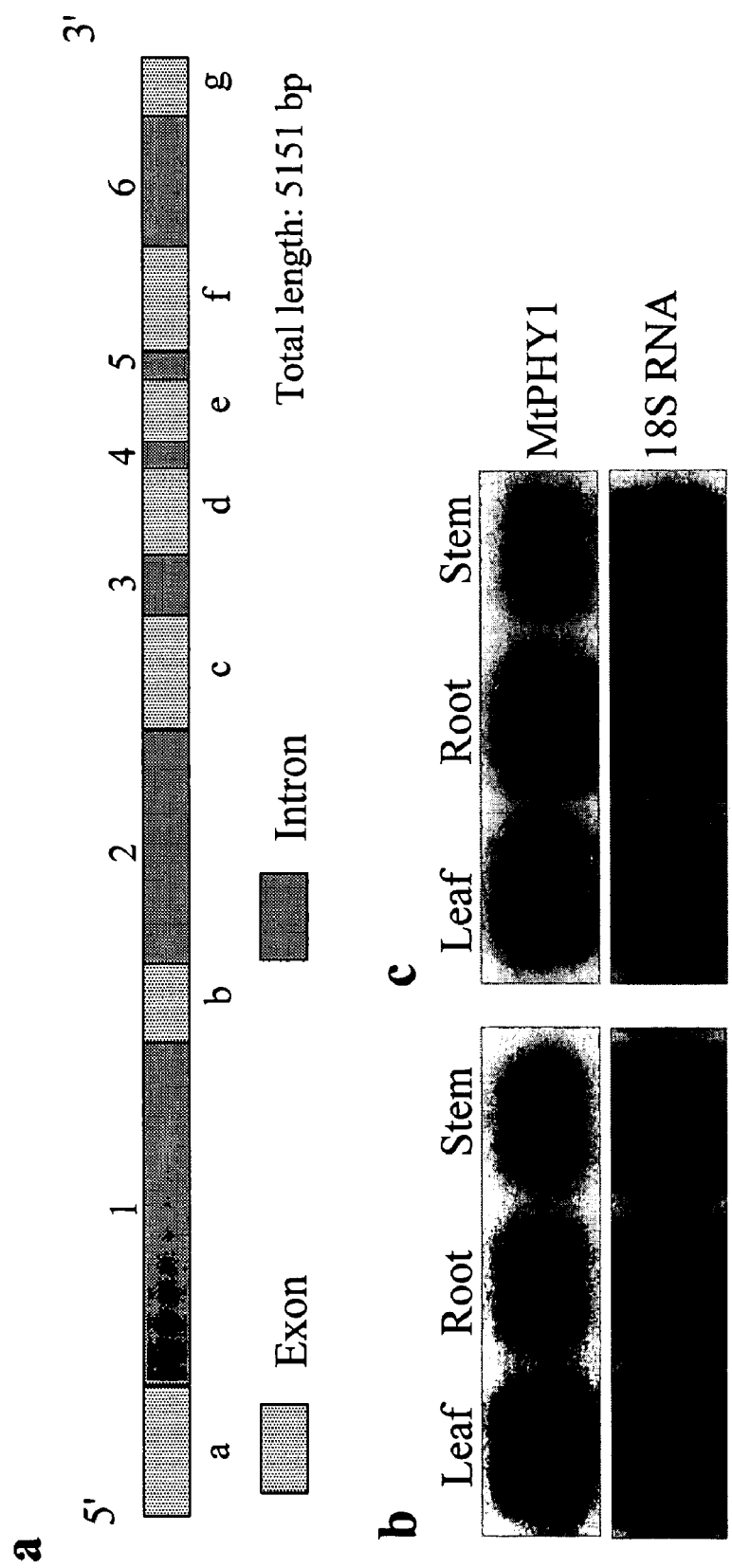
FIG. 1a-b

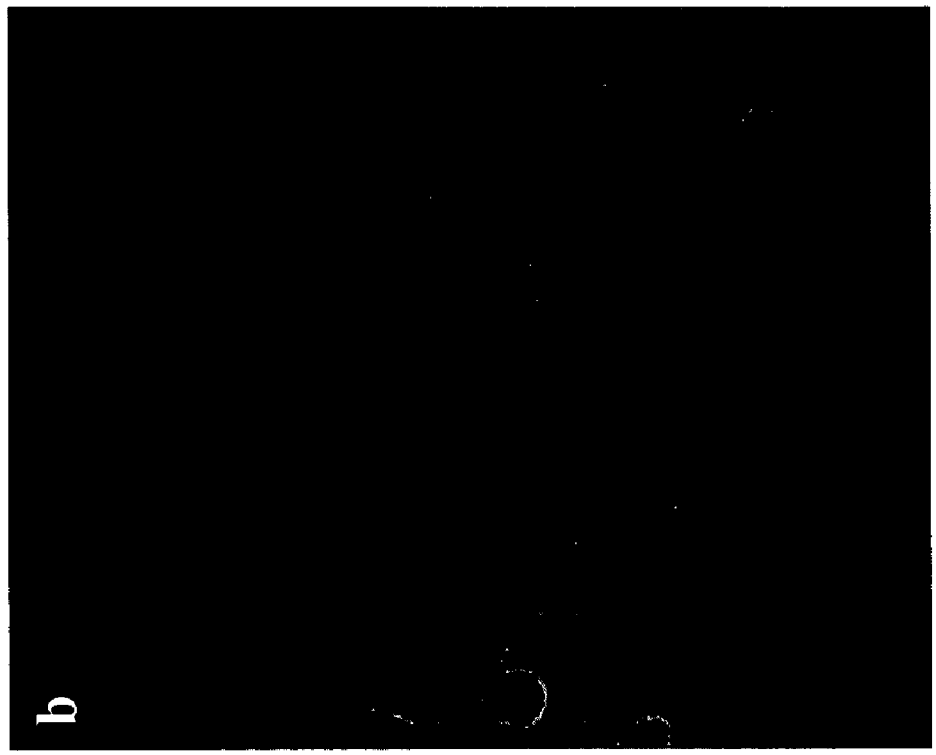
FIG. 2a-b

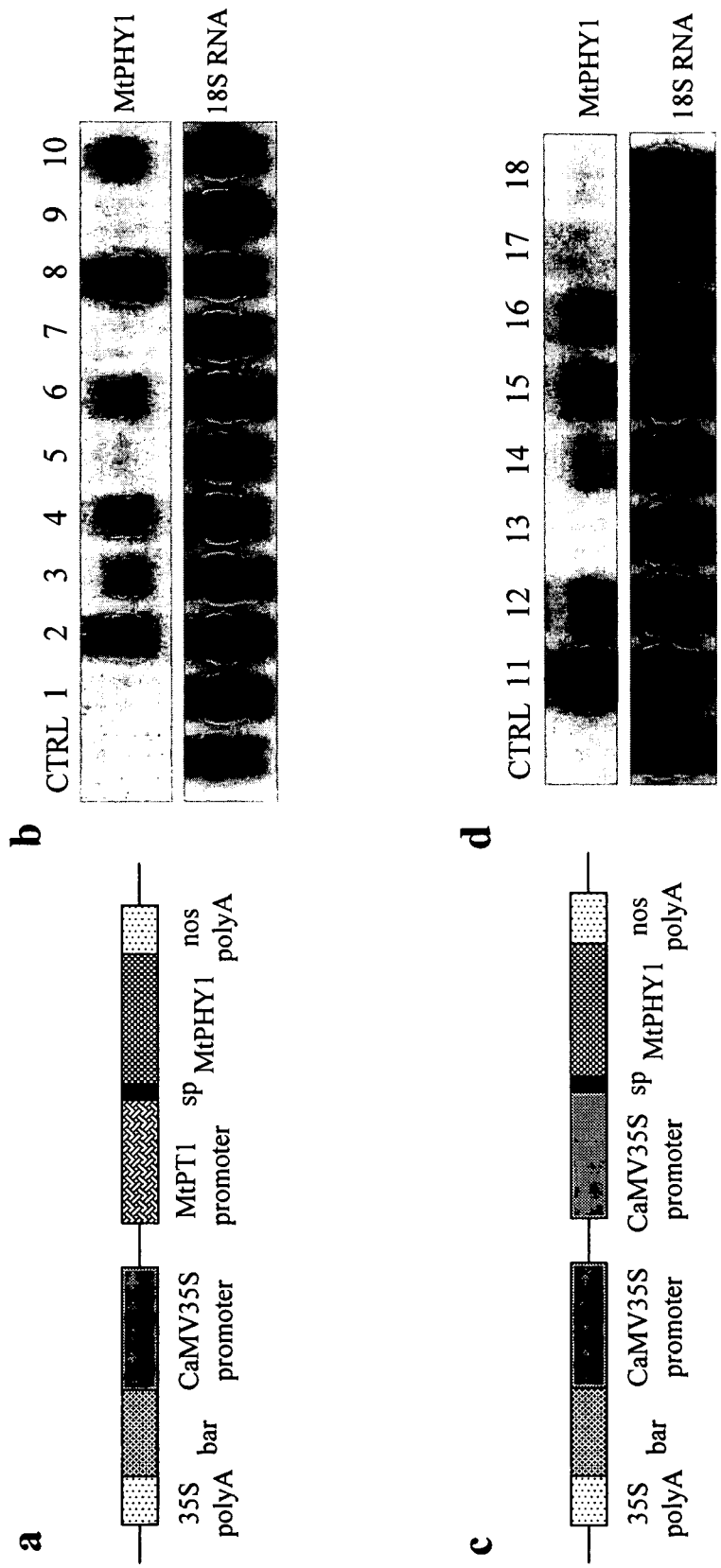
FIG. 3a-d

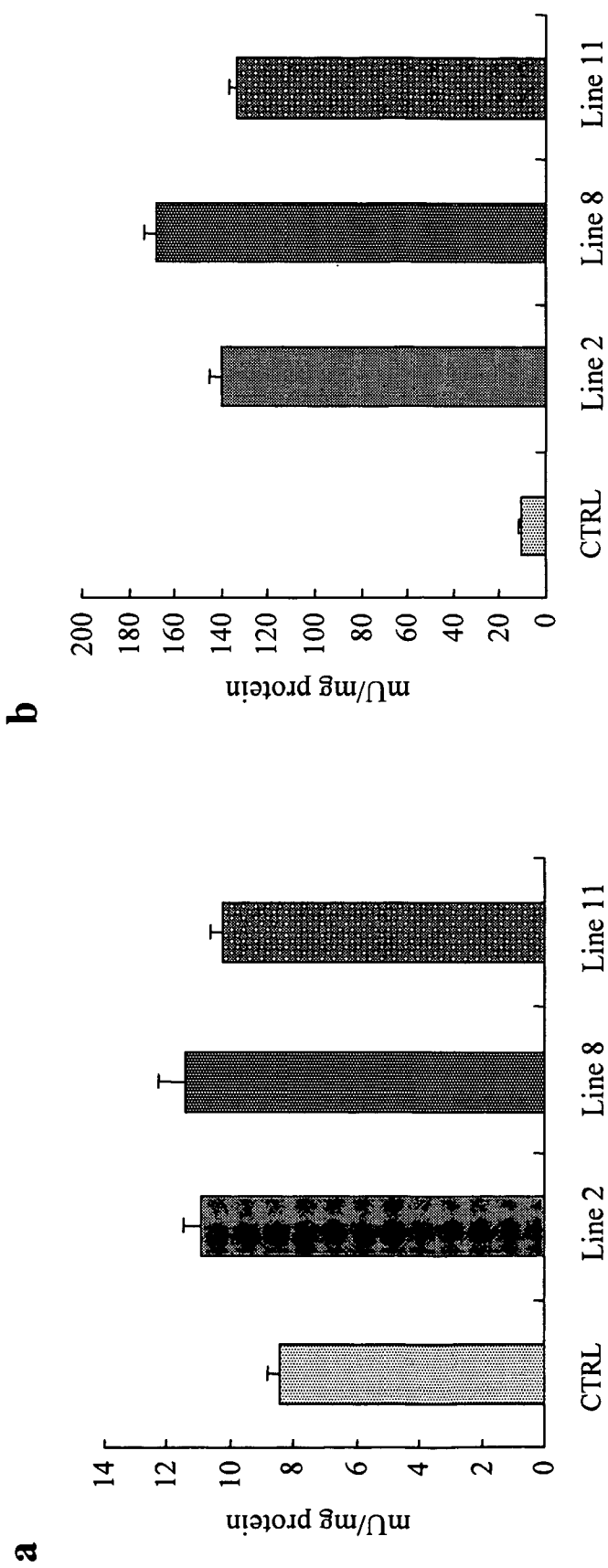
FIG. 4a-b

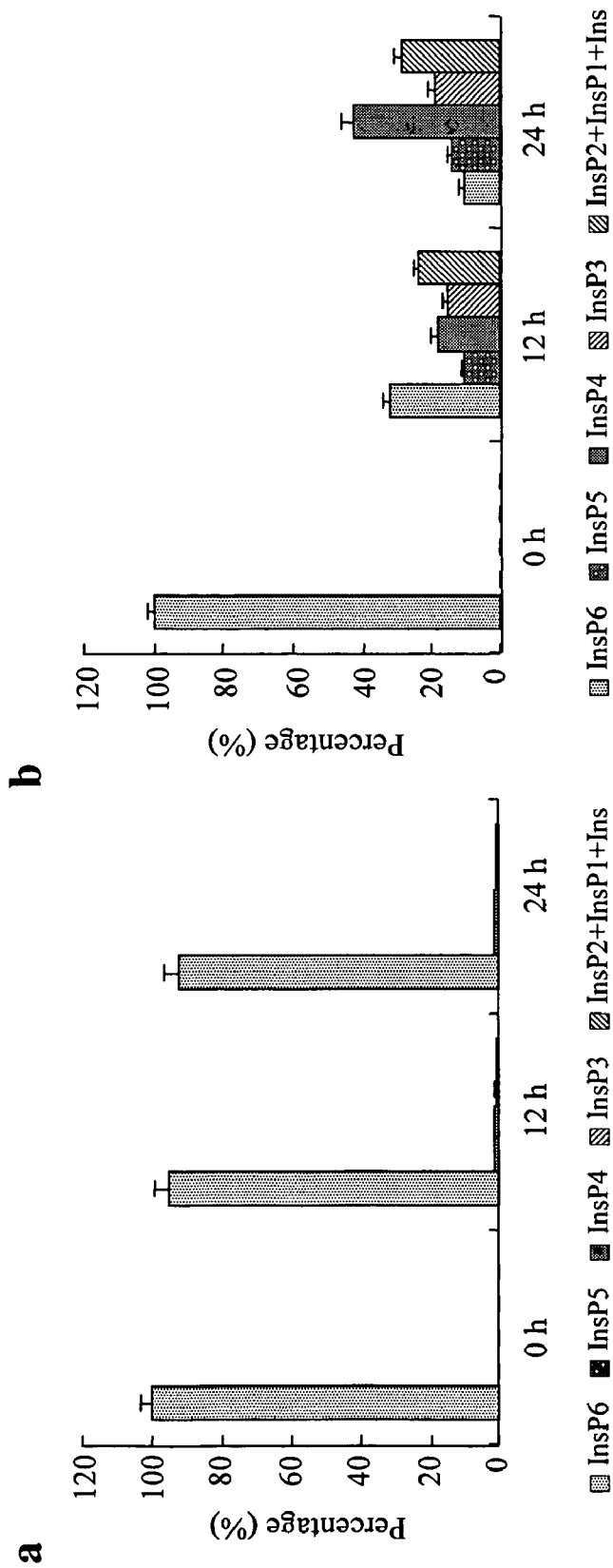
FIG. 5a-b

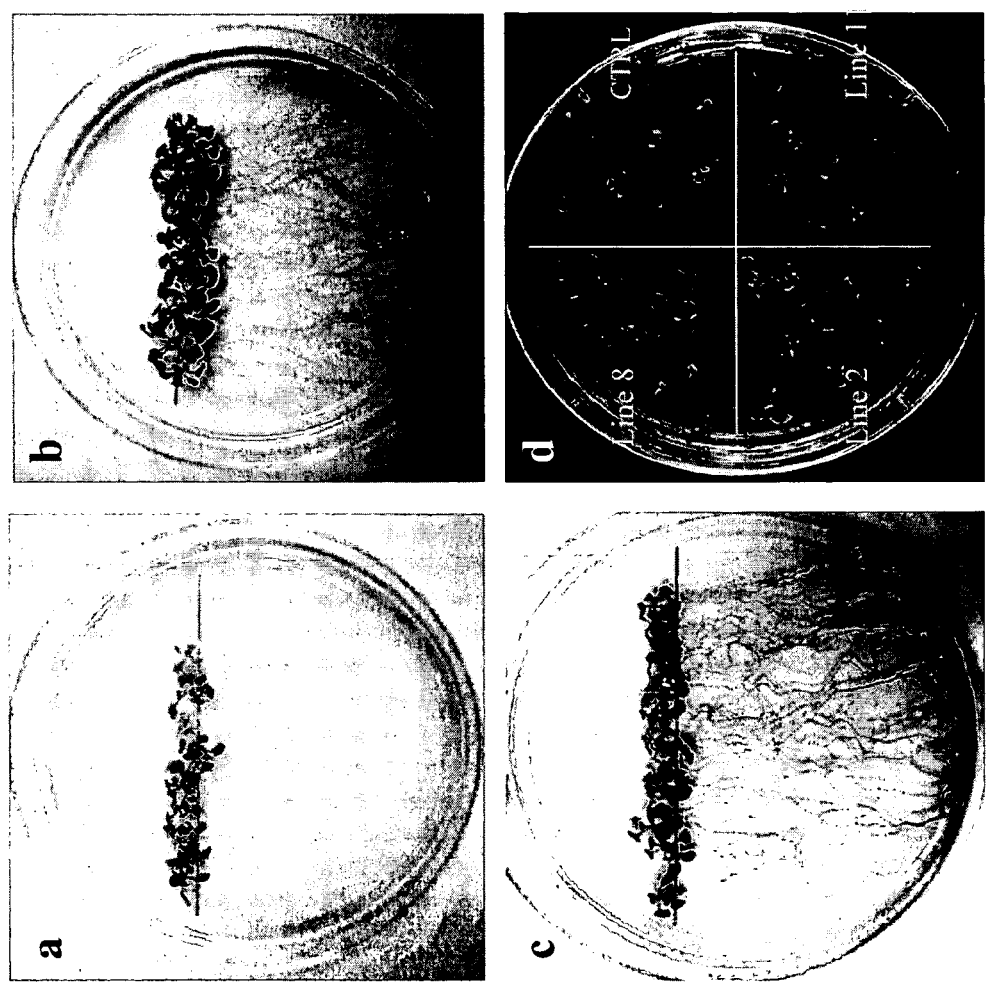
FIG. 6a-d

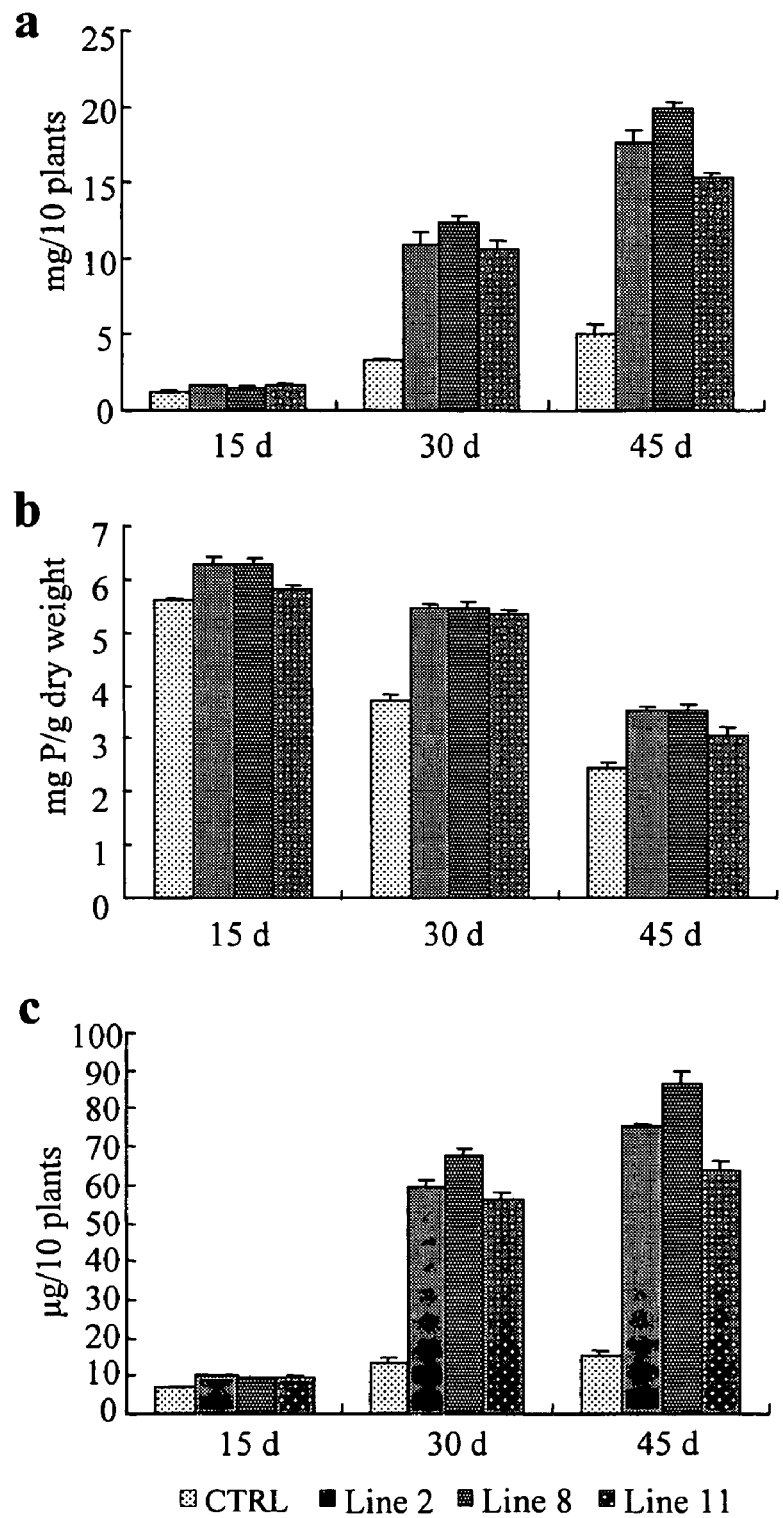
FIG. 7a-c

SEQUENCE LISTING

<160> NUMBER OF SEQ ID NOS: 14

<210> SEQ ID NO 1
<211> LENGTH: 1632
<212> TYPE: DNA
<213> ORGANISM: Medicago truncatula

<400> SEQUENCE: 1

```
atgggttctg ttttggtgca tactcatgtt gttacactgt gtatgttgtt attatcacta      60
agttcaatcc ttgttcatgg tggagttcca accacactgg atggaccttt caagcctgtg     120
acagttcctc tagacaagag cttccgtgga aacgctgtgg acataccaga cacagatcct     180
```

```
cttgttcaaa gaaatgttga agcttttcaa cctgaacaaa tctctctttc actctctacc    240
tcccatgact ctgtttggat tccttggatt acaggagaat tccaaattgg ggagaatata    300
gaaccattag atcctgaaac agttggtagc atagttcaat atggaaggtt tggaaggtca    360
atgaatggcc aagctgttgg ttattccctt gtgtatagtc agctatatcc ttttgaagga    420
cttcagaact atacttctgg aattatacat catgttcgtc tcacaggatt aaagcccaac    480
acactatatc aatatcaatg tggagatcct tctttgtcag caatgagtga tgttcattat    540
ttcagaacaa tgccggtttc aggtcccaag agttaccctg cagaatcgc cgtggttgga    600
gacttaggtc ttacatacaa tacgacatcc actgtcaatc atatgatcag caatcatcct    660
gatcttattc tattggttgg agatgctagt tatgctaaca tgtatcttac taatggcact    720
ggttcagatt gctactcttg ttcatttctct aatactccta tccatgaaac atatcaacca    780
cgttgggatt attggggaag gtacatggaa ccattgattt ccagtgtccc ggtaatggta    840
gtagaaggga atcatgagat agaagaacaa gctgtaaaca agacattcgt tgcttatagt    900
tctcgatttg catttccgtc ggaagagagt gggtcatctt caactttata ttattctttc    960
aatgcgggag gaatacattt tataatgctc ggttcctaca tatcatacga caaatcaggg   1020
gaccagtaca aatggttgga aaggatttg gcttctcttg ataggaagt aactccatgg   1080
ttggtagcta catggcatgc accttggtac agcacttaca agtcacatta tagagaagcg   1140
gagtgtatga gggtcaatat ggaagattta ttatataaat atggtgttga cattgtcttt   1200
aacggacatg ttcatgccta tgagagatcg aaccgtgtat ataactacac attggatccg   1260
tgcggtcctg tttatatcac agttggtgac ggtggtaatc gggaaaagat ggcaattact   1320
catgcagatg aaccaggaaa ctgtcctgaa ccattaacta caccagataa atttatgaga   1380
ggtttctgcg ccttcaattt tacttccggt ccagcagcag gtaaattctg ttgggaccaa   1440
cagcctgatt atagtgcttt tcgcgaaagc agcttcggtc atgggattct agaggtgaag   1500
aatgaaactc atgccttatg gagttggaac cgcaatcaag actattatgg aactgctggt   1560
gatgaaattt acattgttag gcaacctgat aagtgtccac cagttatgcc agaggaggca   1620
cataatacat ga                                                       1632
```

<210> SEQ ID NO 2
<211> LENGTH: 543
<212> TYPE: PRT
<213> ORGANISM: Medicago truncatula

<400> SEQUENCE: 2

Met Gly Ser Val Leu Val His Thr His Val Thr Leu Cys Met Leu
1               5                   10                  15

Leu Leu Ser Leu Ser Ser Ile Leu Val His Gly Gly Val Pro Thr Thr
            20                  25                  30

Leu Asp Gly Pro Phe Lys Pro Val Thr Val Pro Leu Asp Lys Ser Phe
        35                  40                  45

Arg Gly Asn Ala Val Asp Ile Pro Asp Thr Asp Pro Leu Val Gln Arg
    50                  55                  60

Asn Val Glu Ala Phe Gln Pro Glu Gln Ile Ser Leu Ser Leu Ser Thr
65                  70                  75                  80

Ser His Asp Ser Val Trp Ile Ser Trp Ile Thr Gly Glu Phe Gln Ile
                85                  90                  95

Gly Glu Asn Ile Glu Pro Leu Asp Pro Glu Thr Val Gly Ser Ile Val
            100                 105                 110

-continued

```
Gln Tyr Gly Arg Phe Gly Arg Ser Met Asn Gly Gln Ala Val Gly Tyr
            115                 120                 125
Ser Leu Val Tyr Ser Gln Leu Tyr Pro Phe Glu Gly Leu Gln Asn Tyr
        130                 135                 140
Thr Ser Gly Ile Ile His Val Arg Leu Thr Gly Leu Lys Pro Asn
145                 150                 155                 160
Thr Leu Tyr Gln Tyr Gln Cys Gly Asp Pro Ser Leu Ser Ala Met Ser
                165                 170                 175
Asp Val His Tyr Phe Arg Thr Met Pro Val Ser Gly Pro Lys Ser Tyr
            180                 185                 190
Pro Ser Arg Ile Ala Val Val Gly Asp Leu Gly Leu Thr Tyr Asn Thr
        195                 200                 205
Thr Ser Thr Val Asn His Met Ile Ser Asn His Pro Asp Leu Ile Leu
    210                 215                 220
Leu Val Gly Asp Ala Ser Tyr Ala Asn Met Tyr Leu Thr Asn Gly Thr
225                 230                 235                 240
Gly Ser Asp Cys Tyr Ser Cys Ser Phe Ser Asn Thr Pro Ile His Glu
                245                 250                 255
Thr Tyr Gln Pro Arg Trp Asp Tyr Trp Gly Arg Tyr Met Glu Pro Leu
            260                 265                 270
Ile Ser Ser Val Pro Val Met Val Val Glu Gly Asn His Glu Ile Glu
        275                 280                 285
Glu Gln Ala Val Asn Lys Thr Phe Val Ala Tyr Ser Ser Arg Phe Ala
    290                 295                 300
Phe Pro Ser Glu Glu Ser Gly Ser Ser Ser Thr Leu Tyr Tyr Ser Phe
305                 310                 315                 320
Asn Ala Gly Gly Ile His Phe Ile Met Leu Gly Ser Tyr Ile Ser Tyr
                325                 330                 335
Asp Lys Ser Gly Asp Gln Tyr Lys Trp Leu Glu Lys Asp Leu Ala Ser
            340                 345                 350
Leu Asp Arg Glu Val Thr Pro Trp Leu Val Ala Thr His Ala Pro
        355                 360                 365
Trp Tyr Ser Thr Tyr Lys Ser His Tyr Arg Glu Ala Glu Cys Met Arg
    370                 375                 380
Val Asn Met Glu Asp Leu Leu Tyr Lys Tyr Gly Val Asp Ile Val Phe
385                 390                 395                 400
Asn Gly His Val His Ala Tyr Glu Arg Ser Asn Arg Val Tyr Asn Tyr
                405                 410                 415
Thr Leu Asp Pro Cys Gly Pro Val Tyr Ile Thr Val Gly Asp Gly Gly
            420                 425                 430
Asn Arg Glu Lys Met Ala Ile Thr His Ala Asp Glu Pro Gly Asn Cys
        435                 440                 445
Pro Glu Pro Leu Thr Thr Pro Asp Lys Phe Met Arg Gly Phe Cys Ala
    450                 455                 460
Phe Asn Phe Thr Ser Gly Pro Ala Ala Gly Lys Phe Cys Trp Asp Gln
465                 470                 475                 480
Gln Pro Asp Tyr Ser Ala Phe Arg Glu Ser Ser Phe Gly His Gly Ile
                485                 490                 495
Leu Glu Val Lys Asn Glu Thr His Ala Leu Trp Ser Trp Asn Arg Asn
            500                 505                 510
Gln Asp Tyr Tyr Gly Thr Ala Gly Asp Glu Ile Tyr Ile Val Arg Gln
        515                 520                 525
```

-continued

```
Pro Asp Lys Cys Pro Pro Val Met Pro Glu Glu Ala His Asn Thr
    530                 535                 540
```

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
tcctcccgca ttgaaagaat aat                                          23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
agaagttata tgaacccact tg                                           22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
aatataacca acagtataca ctg                                          23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tgtcgacaat gggttctgtt ttgg                                         24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
tccatgggac atgtattatg tgcct                                        25

<210> SEQ ID NO 8
<211> LENGTH: 24
<212> TYPE: DNA
<213> ORGANISM: Artificial Sequence
<220> FEATURE:
```

-continued

```
<223> OTHER INFORMATION: Description of Artificial Sequence:  Synthetic
      Primer

<400> SEQUENCE: 8
tccatgggtt ctgttttggt gcat                                            24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
aggtaacctg aaatgtcagg gatga                                           25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
tggatccatg catgggctgg agtt                                            24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
tccatggctg aatttgttac ctagt                                           25

<210> SEQ ID NO 12
<211> LENGTH: 1533
<212> TYPE: DNA
<213> ORGANISM: Medicago truncatula

<400> SEQUENCE: 12
gctggagttc gaatcccgaa caccccactt ctccacattt aaaatgtgtg aactcaagtc      60
actatgttat ttgaccaaaa aaacaaaatg agaaaaaaaa agaccaagcg gggaaaagta     120
cccatttacc aagtcgatac aaatactaat tgacttttat ttttggtta aaaataataa     180 ttgactttt ttaggggaaa taataataat tgacatttt tttttaatat ttttgacaaa     240
aaattgactt tatgtaccga ttataattat cataaaccca cataatataa cgtcatagtt    300
taattgacag ttggtctgaa acaaaatata gtttaacttg ttagtttttt tagaggagtt    360
aaattgccag ttggttgcat tgcataatat ggcgcatgca cgagttgata tatactattt    420
gatttgataa gagtatacga tacttgtacg ttttgtactt gtgatatatt atgttattgc    480
ggaatatttt atgaaaaaat ttatggttga cattcaaact aaaatgttta cttaatggta    540
gagttataaa cctcgggtcc gcgtaagcat agctcagttg cagagacat gcattattat    600 atgtaggggc tggggttcaa accccggaca ccccacttat tcatcttgaa aaatatgaat    660
```

```
tctaaccact aaattacttg accaaaataa cccaaaatcc tgatgtagga gatcctctga    720
ttaatgtata attttgaaa gaatgtataa catatagttg aatattaggt tgcaacagat    780
acaaggggta ttaaatatat tgagcatatc ctcaagtgga atcaatgtca aatctgaaat    840
atcgtttaat ttccttaacg gatgtcctat atttttcatt ggttatgtct atgtattaag    900
aatatattac ttaaaaacta taaattaatt agagtccaac ttaaaatttt attaagttac    960
aaaaaatagt gcttgtgaag cgttgacatt ggtgaatgct tatgattaat taggcatata   1020
ccccattgat gctaaattga ttcttttga ctttggatgc attcctgatt tggctaggat   1080
tgttacctat atatagctga gtttgattat ctgctcacag tgtgcataaa cctagcttct   1140
cataccactt tacttcttta tcaacttggc ttcttgcaag aggtacgaac tctatctatc   1200
tcccttattg agtttgtaga caccaaatga gtattcatgt tgtacatttt tttttggcaa   1260
atcttggtcg catcatacaa ctgtagagat taatggctcg agataactaa gatatattta   1320
aagagtttag tactcgagtg tatgtgtgta taaaaatata tataattttc attggtatta   1380
ggcacaattt aggtaggtta ctttatagtt ttgagcagtt tatccatttc ttacctcagc   1440
ctcacaaatg tcaagttagt ttttttttg tttactaata tttaatgtgt cttgtgctta   1500
attatgcagg gaaaaactag gtaacaaatt cag                               1533

<210> SEQ ID NO 13
<211> LENGTH: 1238
<212> TYPE: DNA
<213> ORGANISM: Medicago truncatula

<400> SEQUENCE: 13
ccacttgtct ttatttttta agggcaggga ccaccttgtt atttgcttaa aattgaacga     60
aaatattaag attatagtct ctttaggatt acttaaaaaa tcaacaagca aactatgaat    120
ggataattta tgatatagca taatagaaac tattatacaa acccagaatt ttgttattgg    180
agaacctcta actaccagta tagttgaata ttgggttgca acagatacaa ggggtattaa    240
atatattgag catatatctg tttccacaag tggaatcaat gtcaaatcta aaaaatatct    300
cttaattacc ttaagtggaa tggatgtcct agatttttaa ttggttatgt atctgtatta    360
aggatatatt actcggaaag aataaaattag catgtgaact attatagttc cctaaaaaaa    420
aaagtcaact attatagtgg ttttcctcta aaaagagag taaattacac ttcgctttcc    480
ttacagatgt ttgaattact gttccatctc ctcttatatt aaaatataca ttttattctc    540
ctcttattca aaacatatta tgctaaaaaa aaaatctatt agggattttg aatcgttgaa    600
caacataatt gttttactta agtcttaagg tgtttaaatc tctttaggtc aacatcccga    660
aattatgctt aagcatgttt aaatttgtga ttaatgaaat tactttggtg attagctagt    720
gaatttcaac tcttgatata tccaatagca attgccgcaa aagttgtata aatttagttg    780
tacaaatatc atttatctat aatacatttt tcattcctaa ttttatatca aataaacatg    840
gttggatgca agtgatttac atgtgttttcc tattatttat ttacatttt tattacaatg    900 atgtatgtgt ttctgttaat gttgaatgct tagggtatcc aagtttaatc attaattaac    960
ataactagca ttcagattta agaaacaaga aaattaatta aaaaaaaaat agtgcttata   1020
aagcgtttac attgatgaat gcttgtgagt ggtgattagg ttaggcatat accattgatg   1080
ctgaattgat tccttgacc tagcaaggtt catgttacct atatatatgc atattaatag   1140
tttagctgct caaagtgcag gcacctagct agctcctcat acaaacttga cttctcacaa   1200
```

-continued

```
ggaggtcttc tctctctcta tctctctagc ttggggac                    1238

<210> SEQ ID NO 14
<211> LENGTH: 1632
<212> TYPE: DNA
<213> ORGANISM: Medicago truncatula

<400> SEQUENCE: 14
atgggttctg ttttggtgca tactcatgtt gttacactgt gtatgttgtt attatcacta      60
agttcaatcc ttgttcatgg tggagttcca accacactgg atggaccttt caagcctgtg     120
acagttcctc tagacaagag cttccgtgga aacgctgtgg acataccaga cacagatcct     180
cttgttcaaa gaaatgttga agcttttcaa cctgaacaaa tctctctttc actctctacc     240
tcccatgact ctgtttggat ttcttggatt acaggagaat tccaaattgg ggagaatata     300
gaaccattag atcctgaaac agttggtagc atagttcaat atggaaggtt tggaaggtca     360
atgaatggcc aagctgttgg ttattccctt gtgtatagtc agctatatcc ttttgaagga     420
cttcagaact atacttctgg aattatacat catgttcgtc tcacaggatt aaagcccaac     480
acactatatc aatatcaatg tggagatcct tctttgtcag caatgagtga tgttcattat     540
ttcagaacaa tgccggtttc aggtcccaag agttacccta gcagaatcgc cgtggttgga     600
gacttaggtc ttacatacaa tacgacatcc actgtcaatc atatgatcag caatcatcct     660
gatcttattc tattggttgg agatgctagt tatgctaaca tgtatcttac taatggcact     720
ggttcagatt gctactcttg ttcattttct aatactccta tccatgaaac atatcaacca     780
cgttgggatt attggggaag gtacatggaa ccattgattt ccagtgtccc ggtaatggta     840
gtagaaggga atcatgagat agaagaacaa gctgtaaaca agacattcgt tgcttatagt     900
tctcgatttg catttccgtc ggaagagagt gggtcatctt caactttata ttattctttc     960
aatgcgggag gaatacattt tataatgctc ggttcctaca tatcatacga caaatcaggg    1020
gaccagtaca aatggttgga gaaggatttg gcttctcttg atagggaagt aactccatgg    1080
ttggtagcta catggcatgc accttggtac agcacttaca agtcacatta tagagaagcg    1140
gagtgtatga gggtcaatat ggaagattta ttatataaat atggtgttga cattgtcttt    1200
aacggacatg ttcatgccta tgagagatcg aaccgtgtat ataactacac attggatccg    1260
tgcggtcctg tttatatcac agttggtgac ggtggtaatc gggaaaagat ggcaattact    1320
catgcagatg aaccaggaaa ctgtcctgaa ccattaacta caccagataa atttatgaga    1380
ggtttctgcg ccttcaattt tacttccggt ccagcagcag gtaaattctg ttgggaccaa    1440
cagcctgatt atagtgcttt tcgcgaaagc agcttcggtc atgggattct agaggtgaag    1500
aatgaaactc atgccttatg gagttggaac cgcaatcaag actattatgg aactgctggt    1560
gatgaaattt acattgttag gcaacctgat aagtgtccac cagttatgcc agaggaggca    1620
cataatacat ga                                                         1632
```

PLANT PHYTASE GENES AND METHODS OF USE

This application claims the priority of U.S. Provisional Appl. Ser. No. 60/669,318, filed Apr. 7, 2005, the entire disclosure of which is incorporated herein by reference.

BACKGROUND OF THE INVENTION

1. Field of the Invention

The present invention relates generally to the field of molecular biology. More specifically, the invention relates to plant genes involved in phosphorous uptake and methods of use thereof.

2. Description of the Related Art

Phosphate (Pi) is one of the key substrates in energy metabolism and biosynthesis of nucleic acids and membranes. It also plays an important role in photosynthesis, respiration and regulation of a number of enzymes (Raghothama, 1999). While it is a critical macronutrient for plant growth and development, most of the total soil phosphorus (P) is not available for uptake due to its rapid immobilization by soil organic and inorganic components (Von Uexküll and Mutert, 1995; Whitelaw, 2000). Phosphorus is limiting for crop yield on over 30% of the world's arable land, and by some estimates, world resources of inexpensive rock phosphate may be depleted by 2050 (Vance et al., 2003). The lack of inexpensive P has been recognized as a potential future crisis in agriculture (Abelson, 1999). In consideration of the trend toward sustainability and environmental stewardship, P has been a key nutrient in maintaining long-term productivity of agricultural systems (Iyamuremye and Dick, 1996).

The P cycle can be characterized as the flow of P between plants, animals, microorganisms and solid phases of the soil (Iyamuremye and Dick 1996). A significant proportion of the soil P is in organic forms, either as specific organic P compounds or as organic compounds to which inorganic P is linked (Larsen 1967; Bieleski 1973). Organic P generally makes up 20% to 80% of the total P in the surface layer of the soil, which, after mineralization, can contribute considerably to the P nutrition of plants (Dalal 1977; Iyamuremye and Dick 1996). The predominant form of organic P is phytate (inositol hexa- and penta-phosphates), which composes up to 60% of soil organic P and is poorly utilized by plants (Iyamuremye and Dick 1996; Mudge et al., 2003).

Phytate can be hydrolyzed to inorganic phosphate (Pi) and myo-inositol through the action of phytase enzymes (Mudge et al., 2003). In the study of phytases, much attention has been paid to the use of phytases as an animal feed additive, because phytate in plant seeds is largely indigestible by monogastric animals (reviewed by Wodzinski and Ullah 1996; Brinch-Pedersen et al., 2002; Vohra and Satyanarayana 2003). Phytases have been commercially produced based on the filamentous fungus *Aspergillus niger* (Brinch-Pedersen et al., 2002). By comparison, phytases in plant roots have received much less attention; the potential of producing phytase in plant roots for improved P uptake has only been recognized in recent years. Application of a fungal phytase to sterile cultures of subterranean clover (*Trifolium subterraneum*) enabled the seedlings to use phytate as the only source of P (Hayes et al., 2000). Ectopic expression of a fungal phytase gene (Richardson et al., 2001; Mudge et al., 2003) or a synthetic phytase gene (Zimmermann et al., 2003) resulted in increased P acquisition and biomass production in transgenic plants.

Phytases have been identified in roots of plants (Hübel and Beck 1996; Li et al., 1997; Hayes et al., 1999; Richardson et al., 2000) such as maize (Maugenest et al., 1997; Maugenest et al., 1999) and soybean (Hegeman and Grabau 2001). (Hübel and Beck 1996; Li et al., 1997; Hayes et al., 1999; Richardson et al., 2000). However, it has been suggested that the activity of these enzymes in roots is inadequate for effective utilization of organic P (Hayes et al., 1999; Richardson et al., 2000; Brinch-Pedersen et al., 2002). Additionally, in these plants phytases do not appear to be secreted or involved in P acquisition of roots from external phytate (Hübel and Beck 1996; Maugenest et al., 1999; Hegeman and Grabau 2001). To date, there have been no reports on improving P uptake by transgenically expressing any phytase genes of plant origin. There is, therefore, a great need in the art for new genes capable of improving P utilization.

SUMMARY OF THE INVENTION

In one aspect, the invention provides an isolated nucleic acid sequence encoding a plant phytase conferring the ability to hydrolyze phytate. In certain embodiments, the nucleic acid sequence may be further defined as selected from the group consisting of: (a) a nucleic acid sequence encoding the polypeptide of SEQ ID NO:2; (b) a nucleic acid sequence comprising the sequence of SEQ ID NO:1; (c) a nucleic acid sequence hybridizing to SEQ ID NO:1 under conditions of 0.15 M NaCl and 70° C.; (d) a nucleic acid sequence comprising at least 85% sequence identity, including at least 90%, 95% and 98% identity, over the full length the nucleic acid sequence of SEQ ID NO:1; and (e) a nucleic acid sequence complementary to the nucleic acid sequence of (a), (b), (c) or (d).

In yet another aspect, the invention provides a recombinant vector comprising an isolated nucleic acid sequence of the invention. The nucleic acid sequence may be in sense orientation. In certain embodiments, the recombinant vector may further comprise at least one additional sequence chosen from the group consisting of: a regulatory sequence, a selectable marker, a leader sequence and a terminator. In further embodiments, the additional sequence is a heterologous sequence and the promoter may be constitutive, developmentally-regulated, organelle-specific, inducible, inducible, tissue-specific, constitutive, cell-specific, seed specific, or germination-specific promoter. The recombinant vector may or may not be an isolated expression cassette.

In still yet another aspect, the invention provides an isolated polypeptide comprising the amino acid sequence of SEQ ID NO:2, or a fragment thereof having phytase activity; and including sequences with at least 85% sequence identity to SEQ ID NO:2, including at least 90%, 95% and 98% identity, to this sequence.

In still yet another aspect, the invention provides a transgenic plant transformed with a selected DNA comprising a nucleic acid sequence of the invention encoding phytase activity and conferring increased phosphorous uptake. The transgenic plant may be a monocotyledonous or dicotyledonous plant and may be a legume. The plant may also be an $R_0$ transgenic plant and/or a progeny plant of any generation of an $R_0$ transgenic plant, wherein the transgenic plant has inherited the selected DNA from the $R_0$ transgenic plant.

In still yet another aspect, the invention provides a seed of a transgenic plant of the invention, wherein the seed comprises the selected DNA. The invention also provides a host cell transformed with such a selected DNA. The host cell may express a protein encoded by the selected DNA. The cell may have inherited the selected DNA from a progenitor of the cell and may have been transformed with the selected DNA. The cell may be a plant cell.

In still yet another aspect, the invention provides a method of increasing plant phosphorous utilization comprising introducing into the plant a nucleic acid encoding phytase. In a method of the invention, up-regulating phytase may be carried out by introducing a recombinant vector of the invention into a plant. The vector may be introduced by plant breeding and/or direct genetic transformation.

In still yet another aspect, the invention provides a method of making food for human or animal consumption comprising: (a) obtaining a plant of the invention; (b) growing the plant under plant growth conditions to produce plant tissue from the plant; and (c) preparing food for human or animal consumption from the plant tissue. In the method, preparing food may comprise harvesting plant tissue. In certain embodiments, the food is starch, protein, meal, flour or grain.

In still yet another aspect, the invention provides a method for bioremediation of phosphorous comprising: (a) identifying a soil and/or water sample in need of bioremediation for phosphorous; (b) obtaining a transgenic plant expressing a heterologous nucleic acid sequence encoding phytase, wherein the transgenic plant expresses the nucleic acid sequence and exhibits increased soil phosphorous uptake relative to a plant of the same genotype lacking the nucleic acid sequence; and (c) growing the roots of the plant in the presence of the soil/and or water to allow the plant to bioremediate the phosphorous.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1: a: Diagram of the structure of the MtPHY1 gene based on analysis of the genomic DNA sequences. Exons a, b, c, d, e, f and g are at positions 1-556, 557-751, 752-1084, 1085-1300, 1301-1491, 1492-1777 and 1778-1893 of the cDNA, respectively. Introns 1, 2, 3, 4, 5 and 6 are 1447 bp, 1054 bp, 140 bp, 81 bp, 80 bp and 365 bp in length, respectively. b: northern hybridization analysis of different organs of *M. truncatula* under high (2 mM) Pi conditions. c: northern hybridization analysis of different organs of *M. truncatula* under low (10 μM) Pi conditions. The 3' UTR of MtPHY1 cDNA was used as probe.

FIG. 2: a: Subcellular localization of MtPHY1-GFP fusion protein in roots of transgenic *Arabidopsis* carrying the gene construct CaMV35S::MtPHY1-GFP. Arrow shows the detection of green fluorescence in the apoplast. b: Transgenic root carrying the gene construct CaMV35S::GFP as control. Green fluorescence is evident in the cytoplasm and nucleus.

FIG. 3: a: Schematic illustration of the MtPT1::MtPHY1 gene construct used for generating transgenic *Arabidopsis* plants. b: northern hybridization analysis of transgenic *Arabidopsis* carrying the gene construct MtPT1::MtPHY1. CTRL lane represents control. Lanes 1-10 represent ten homozygous transgenic lines carryng MtPT1::MtPHYL1. c: schematic illustration of the CaMV35S::MtPHY1 gene construct used for generating transgenic *Arabidopsis* plants. d: northern hybridization analysis of transgenic *Arabidopsis* carrying the gene construct CaMV35S::MtPHY1. CTRL lane represents control. Lanes 11-18 represent eight homozygous transgenic lines carrying CaMV35S::MtPHY1.

FIG. 4: a: Phytase activities in whole root extracts of transgenic *Arabidopsis* lines growing in agar medium with phytate as the sole source of P. b: Phytase activities in root apoplast of transgenic *Arabidopsis* lines growing in agar medium with phytate as the sole source of P. CTRL: empty vector control, lines 2 and 8 carried the transgene MtPT1::MtPHY1, line 11 carried the transgene CaMV35S::MtPHY1. Data are presented as the mean±SE of three individual assays.

FIG. 5: a, b: Intermediates of phytate (InsP6) degradation by root exudates of empty vector control (a) and transgenic line 8 (b) in liquid culture medium with phytate as the sole source of P. Data are presented as the mean±SE of three individual assays.

FIG. 6: a-c: Staining of phosphomonoesterase activity in roots of *Arabidopsis* growing in agar medium with phytate as the sole source of P. a: Empty vector control. b: Transgenic line 8 carrying the gene construct MtPT1::MtPHY1. c: Transgenic line 11 carrying the gene construct CaMV35S::MtPHY1. The dark, purple color indicates enzyme activity in roots and root exudates. d: Phenotype of transgenic *Arabidopsis* plants growing in MS agar medium with phytate as the sole source of P. CTRL: empty vector control, lines 2 and 8 carried the transgene MtPT1::MtPHY1, line 11 carried the transgene CaMV35S::MtPHY1. The plants from different lines were firstly germinated and grown on normal MS agar medium for 8 days and then transferred to modified MS medium in which Pi was replaced by phytate and grown for two more weeks.

FIG. 7: a: Dry weight of the shoots of the transgenic *Arabidopsis* lines growing in agar medium with phytate as the sole source of P. b: Pi concentration of transgenic *Arabidopsis* lines growing in agar medium with phytate as the sole source of P. c: Total P content of transgenic *Arabidopsis* lines growing in agar medium with phytate as the sole source of P. CTRL: empty vector control, lines 2 and 8 carried the transgene MtPT1::MtPHY1, line 11 carried the transgene CaMV35S::MtPHY1. The plants from different lines were firstly germinated and grown on normal MS agar medium for 8 days and then transferred to modified MS medium in which Pi was replaced by phytate. Measurements were recorded when the plants were 15-, 30- and 45-days old. Data are presented as the mean±SE of six replicates per line.

DETAILED DESCRIPTION OF THE INVENTION

The invention overcomes the limitations of the prior art by providing plant genes such that, when expressed heterologously, the phytase is secreted and mediates increased phosphorous (P) bioavailability. The inventors demonstrate in one embodiment that overexpression of phytase increases breakdown of phytate into inorganic P that can be used by plants. Since P in the form of phytate is normally largely inaccessible to plants, this expands the opportunities for engineering and breeding plants that are less dependent on phosphates provided by fertilizers. Phosphorus is one of the least-available nutrients in soils, and therefore this represents a significant advance to agriculture and the environment in general. Increased P-bioavailability may be implemented both to increase crop yields in P-deficient environments and to minimize reliance on fertilizers, which can leach in rainwater runoff and represent a significant environmental problem.

In one example, the inventors have demonstrated the characterization and transgenic expression of a novel phytase gene that was designated MtPHY1 and originally isolated from *Medicago truncatula*. Overexpression of a MtPHY1-GFP fusion protein in *Arabidopsis thaliana* demonstrated that MtPHY1 is secreted and localized primarily to the apoplast. This could be attributed to a 27 amino acid N-terminal secretion signal encoded within the MtPHY1 gene. Transgenic *Arabidopsis* plants carrying either of the chimeric MtPHY1 gene constructs showed expression of MtPHY1 RNA, and in each case transgenic *Arabidopsis* lines were isolated that expressed MtPHY1 at high levels. These lines were analyzed for phytate activity, and it was found that root extracts from transgenic plants had 22% to 36% higher activity while activity in the apoplast was 12.3 to 16.2 fold higher in transgenic plants. These data are consistent with the finding that the MTPHY1 encoded protein is secreted. This finding is of great importance since secreted phytase could break down phytate in soils rather than just in the intracellular milieu as is the case with previous plant phytases.

In another example, the inventors have demonstrated the activity of secreted MtPHY1. In these studies, transgenic and control *Arabidopsis* plants were grown in liquid medium containing phytate as the sole source of P. At time intervals, the level of phytate (InsP6) and phytate break-down products InsP5, InsP4, InsP3, InsP2, InsP1 and Ins (indicative of the release of Pi) in the media was analyzed. Results indicated that after 24 hours the liquid medium of control plants contained negligible amounts of phytate break-down products. On the other hand, medium from plants expressing MtPHY1 had little remaining phytate (InsP6) and enhanced amounts of phytate break-down products indicating release of Pi. These studies confirm that secreted phytase from MtPHY1 expressing plants was active against phytate in the surrounding media. Further experiments with transgenic plants grown in agar medium confirmed these results since phytase activity could be detected in the roots and root exudates. Thus, MtPHY1 encoded phytase is active and secreted under conditions that model natural plant growth conditions. Because of the presence of active phytase in the rhizosphere it is contemplated that plants expressing MtPHY1 can be grown adjacent to other crops to increase the general bioavailability of P in a field. Alternatively, by rotating planting of MtPHY1 transgenic plants with that of plants which require Pi, the amount of fertilizer needed to maintain soil P levels could be reduced.

In a further example, the effect of MtPHY1 expression on the growth, and P uptake of transgenic plants was examined. During incubation periods that depleted control plants of Pi reserves, the transgenic plants had dramatically increased growth. For example, after 30 days, dry weight of the transgenic plants was 3.1- to 3.6-fold higher than the control plants. For 45-day-old plants, dry weight of the MtPHY1 expressing plants was 3.1- to 4.0-fold higher than control plants. Increases were also observed in the P content of MtPHY1 transgenic plants, indicating the increased bioavailability of P afforded by MtPHY1 expression. Total P contents in 45-day-old transgenic plants were found to be increased by 4.1- to 5.5-fold. When P levels in plants were normalized to the mass of the plant, significant increases were also observed demonstrating that the observed increases in total P content were not merely due to the size difference between transgenic and control plants. These studies demonstrate the advantages of MtPHY1 expressing transgenic plants when grown in low Pi conditions. Additionally, because the transgenic plants had higher P concentration and drastically increased total P contents, this approach is also applicable to removing excessive organic P from certain land areas. One example is land dumped with poultry litter. The runoff of excessive P in such areas causes environmental concerns regarding pollution of surface or groundwater (Gaston et al., 2003; Pote et al., 2003).

Two chimeric gene constructs were made in which MtPHY1 was expressed from a root-specific promoter or by a constitutive promoter. It may be desired in particular embodiments to use root-specific promoters such as the MtPT1, MtPT2, or MtPT3 (SEQ ID NOs:12 to 14) promoters for transgenic expression of phytase genes. Therefore, the expression of MtPHY1 was compared using either a novel root specific promoter MtPT1 (SEQ ID NO:12) or the constitutive CaMV35S promoter. The MtPT1 promoter mediated expression that was equal to or greater than observed expression from CaMV35S. Expression was similar with either promoter thus, the MtPT1 may be used in order to assure expression specifically in the roots where soil phytate is processed.

In summary, consistent and closely related molecular, biochemical, phenotypic and biomass data demonstrated for the first time that the transgenic expression of a plant secreted phytase gene led to significant improvement in P uptake and plant growth when phytate was supplied as the sole P source. The results demonstrate a valuable approach for improving plant organic P utilization and for bioremediation.

I. Plant Transformation Constructs, Nucleic Acids and Polypeptides

Certain embodiments of the current invention concern plant transformation constructs comprising a phytase coding sequence. An exemplary coding sequence for use with the invention encodes the polypeptide of SEQ ID NO:2. In certain embodiments of the invention, transformation constructs comprise the nucleic acid sequence of SEQ ID NO:1 or derivatives thereof.

Coding sequences may be provided operably linked to a heterologous promoter, in either sense or antisense orientation. Expression constructs are also provided comprising these sequences, including antisense oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

Provided herein are also transformation vectors comprising nucleic acids capable of hybridizing to the nucleic acid sequences, for example, of SEQ ID NO:1. As used herein, "hybridization," "hybridizes" or "capable of hybridizing" is understood to mean the forming of a double or triple stranded molecule or a molecule with partial double or triple stranded nature. Such hybridization may take place under relatively high stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

The invention provides a polynucleotide sequence identical over its entire length to each coding sequence set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

Another aspect of the present invention relates to the polypeptide sequences set forth in the Sequence Listing, as well as polypeptides and fragments thereof, particularly those polypeptides which exhibit phytase activity and also those polypeptides which have at least 85%, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs can be used to determine "identity" between two sequences these programs include but are not limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLAST X program is publicly available from NCBI and other sources (BLAST Manual, Altschul, S., et al., NCBI NLM NIH, Bethesda, Md. 20894; Altschul, S., et al., 1990). The well known Smith Waterman algorithm can also be used to determine identity.

Parameters for polypeptide sequence comparison include the following: Algorithm: Needleman and Wunsch (1970); Comparison matrix: BLOSSUM62 from Hentikoff and Hentikoff, (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for polynucleotide sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

One beneficial use of the sequences provided by the invention will be in the alteration of plant phenotypes by genetic transformation with phytase coding sequences. The phytase coding sequence may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with phytase coding sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant.

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current invention are as follows.

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those promoters associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the CaMV35S promoter is used to express phytase coding sequences.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that phytase coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots. In certain embodiments the root specific MtPT1 MtPT2 or MtPT3 promoters may be used to express phytase coding sequence (SEQ ID NOs:12-14).

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a phytase coding sequence is used. Alternatively, a heterologous 3' end may enhance the expression of sense or antisense phytase coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al, 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

II. Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al, (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by S. hygroscopicus and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) which is encoded by the bar gene in S. hygroscopicus and the pat gene in S. viridochromogenes. The use of the herbicide resistance gene encoding phosphinothricin acetyl transferase (PAT) is referred to in DE 3642 829 A, wherein the gene is isolated from Streptomyces viridochromogenes. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) Brassica (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the EPSPS of Salmonella typhimurium, encoded by the gene aroA. The EPSPS gene from Zea mays was cloned and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected phytase coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VI. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Cloning and Characterization of the *M. truncatula* Phytase Gene, MtPHY1

A full-length cDNA coding for phytase was isolated from *M. truncatula* by 5' RACE and RT-PCR. First, the 5' part of the gene was amplified using the RACE amplification kit (BD Biosciences, Palo Alto, Calif.). A fragment of about 1.2 kb was amplified by 5' RACE with a reverse primer (5'-TCCTC-CCGCATTGAAAGAATAAT-3') (SEQ ID NO:3) specific to an EST clone (NF011E07RT) that represented TC91767. Based on sequence information of the EST clone and the fragment obtained by 5' RACE, a new pair of primers was designed: forward 5'-AGAAGTTATATGAACCCACTTG-3' (SEQ ID NO:4) and reverse 5'-AATATAACCAACAGTATA-CACTG-3' (SEQ ID NO:5). The full-length cDNA was obtained by RT-PCR using the new primer pair. The sequence of the cDNA, designated MtPHY1, was deposited in Genbank (accession number AY878355).

The cloned cDNA (SEQ ID NO:1) is 2067 bp in length containing an open reading frame (ORF) of 1632 bp capable of encoding 543 amino acids (SEQ ID NO:2). A signal peptide of 27 amino acids at the N' end was predicted by SignalP (Nielsen et al., 1997; Bendtsen et al., 2004). Analysis of the predicted MtPHY1 protein sequence by TargetP (Emanuelsson et al., 2000) revealed a secretion pathway score of 0.967, indicating that the protein is likely to be secreted to the outside of the cell.

The predicted MtPHY1 protein shares 71.9% and 71.6% identities with the soybean phytase (AAK49438.1) and an *Arabidopsis* putative purple acid phosphatase (AF448726), respectively. The sequence information of MtPHY1 cDNA was used to blast search genomic sequences of *M. truncatula* (www.genome.ou.edu/*medicago*.html), provided by the Advanced Center for Genome Technology at the University of Oklahoma (Roe and Kupfer 2004). A genomic clone covering the entire MtPHY1 cDNA was identified. The MtPHY1 cDNA sequence was aligned with the genomic sequence by the DNAstar software and information regarding exons and introns was obtained. Genomic sequence analysis indicates that the MTPHY1 gene is 5151 bp long and includes 7 exons interrupted by 6 introns (FIG. 1*a*).

Southern hybridization was carried out to determine the number of copies of the MtPHY1 gene in the *M. truncatula* genome. Briefly, twenty μg of *M. truncatula* genomic DNA was digested with restriction enzymes BamHI, EcoRI, NcoI and SalI and separated through a 0.8% agarose gel. DNA gel blotting was carried out following standard protocols (Sambrook et al., 1989). To avoid cross hybridization of MtPHY1 with other similar sequences, the 3' untranslated region (UTR) was [$^{32}$P] dCTP labeled and used as the probe. Southern hybridizations were performed following the QuikHyb Hybridization protocols (Stratagene, La Jolla, Calif.). Analysis of Southern blot data indicated that there are 1-2 copies of this gene in *M. truncatula* genome (data not shown).

The expression pattern of the MtPHY1 gene was analyzed by northern hybridization with RNA isolated from different tissues of *M. truncatula*. Briefly, *M. truncatula* (ecotype A17) was grown under conditions as described by (Liu et al., 1998). The seeds were treated with concentrated $H_2SO_4$ for 10 min, rinsed three times in sterile water and germinated in pots filled with sterilized fine sand. Seedlings were fertilized with half-strength Hoagland's solution containing either 10 μM (low-Pi) or 2 mM (high-Pi) $KH_2PO_4$ three times a week. After three weeks, the roots, leaves and stems were harvested, frozen in liquid nitrogen and stored at −80° C. for RNA isolation. Total RNA was then isolated using TRI reagent (Molecular Research Center, Inc., Cincinnati, Ohio) and RNA gel blotting was carried out according to standard protocols (Sambrook et al., 1989). For analyzing transcript levels in different organs of *M. truncatula*, the 3' UTR of MtPHY1 was used as the probe. For analyzing expression levels of transgenes in *Arabidopsis* root, the coding sequence of MtPHY1 was used as the probe. Northern hybridizations were performed using [$^{32}$P] dCTP labeled probes following the QuikHyb Hybridization protocols (Stratagene, La Jolla, Calif.).

Results of these analyses indicated that under high-Pi (2 mM) growth conditions, higher level of MtPHY1 transcripts accumulated in the leaf than in the root (FIG. 1*b*). However, under low-Pi (10 μM) conditions, the transcript level was increased in the root, with the strongest hybridization signal detected in the root (FIG. 1*c*).

EXAMPLE 2

Subcellular Localization of MtPHY1

To localize the translated product of the cloned phytase gene, a binary vector (CaMV35S::MtPHY1-GFP) containing an in-frame fusion of MtPHY1 ORF and GFP under the control of CaMV35S promoter was constructed. The CaMV35S::GFP construct was created by inserting a HindIII-EcoRI fragment from the CaMV35S-sGFP(S65T)-nos plasmid (Chiu et al., 1996) into HindIII-EcoRI digested binary vector pCAMBIA3300. For the construction of phytase-GFP fusion vector (CaMV35S::MtPHY1-GFP), the open reading frame (ORF) of MtPHY1 was PCR amplified using high-fidelity Taq polymerase (Stratagene, LA Jolla, Calif.). The primers used for the amplification were 5'-T<u>GTCGAC</u>AATGGGTTCTGTTTTGG-3' (SEQ ID NO:6) (forward) and 5'-T<u>CCATGGG</u>ACATGTATTATGTGCCT-3' (SEQ ID NO:7) (reverse), in which a SalI and an NcoI restriction sites (underlined) were introduced at the 5' and 3' end, respectively. The PCR amplified product was cloned into TA vector (Promega, Madison, Wis.), sequenced, double digested by SalI-NcoI, and inserted in front of the GFP of CaMV35S::GFP without frame shift.

Transgenic *Arabidopsis* plants were generated with CaMV35S::MtPHY1-GFP and CaMV35S::GFP and were grown in MS agar medium with phytate as the sole source of P. GFP fluorescence was then detected and imaged with the Bio-Rad 1024 ES Confocal Laser Scanning Microscope. In lines carrying CaMV35S::MtPHY1-GFP, green fluorescence was mainly detected in the root apoplast (FIG. 2*a*), whereas green fluorescence was freely distributed in cells of the transgenic lines carrying CaMV35S::GFP (FIG. 2*b*). The results indicated that the phytase-GFP fusion protein was transported across the cell membrane and accumulated in the apoplast. Thus the phytase encoded by MtPHY1 is an extracellular protein.

EXAMPLE 3

Transgenic Expression of MtPHY1

For transgenic expression of MtPHY1, chimeric genes were constructed under the control of the constitutive CaMV35S promoter and the root-specific MtPT1 promoter, respectively (FIGS. 3*a* and *c*). For the construction of MtPHY1 under the control of the CaMV35S promoter (CaMV35S::MtPHY1), the ORF of MtPHY1 were PCR amplified using primers 5'-T CCATGGGTTCTGTTTTGGTGCAT- 3' (SEQ ID NO:8) (forward) and 5'-A GGTAACCTGAAATGTCAGGGATGA-3' (reverse) (SEQ ID NO:9). Restriction sites NcoI and BstEII were introduced in the amplified fragment. The fragment was cloned into TA vector, sequenced, double digested by NcoI-BstEII and then introduced into NcoI-BstEII digested binary vector pCAMBIA3301. The root-specific promoter, MtPT1, was isolated from the phosphate transporter 1 gene. For the construction of MtPHY1 under the control of MtPT1 promoter (MtPT1::MtPHY1), the promoter fragment was PCR amplified from *M. truncatula* genomic DNA with primers 5'-T GGATCCATGCATGGGCTGGAGTT-3' (forward) (SEQ ID NO:10) and 5'-TCCATGGCTGAATTTGTTACCTAGT-3' (reverse) (SEQ ID NO:11). Restriction sites BamHI and NcoI were introduced in the amplified promoter fragment. The amplified MtPT1 promoter fragment was cloned into TA vector, double digested by BamHI-NcoI and then inserted into BamHI-NcoI digested CaMV35S::MtPHY1 to replace CaMV35S promoter.

DNA of the newly constructed binary vectors was transferred into the *Agrobacterium tumefaciens* strain C58 by the freeze-thaw method (Chen et al., 1994). Transgenic *Arabidopsis* (ecotype Columbia) plants were produced following the floral dip method (Clough and Bent 1998). Single-copy trangenic plants were identified by Southern hybridization analysis. T3 homozygous lines were obtained after selfing and phosphinothricin (PPT) selection. An empty vector transgenic line, which showed no difference to wild-type plants, was used as control.

Ten T3 homozygous lines carrying MtPT1::MtPHY1 and eight T3 homozygous lines carrying CaMV35S::MtPHY1 were used for further analyses. Northern blot hybridization analysis revealed large differences in transcript levels between the independent transgenic lines (FIGS. 3*b* and *d*). High levels of transgene expression were observed in independent transgenic lines 2, 8 and 11 (FIGS. 3*b* and *d*), and these were chosen for further detailed analysis. Lines 2 and 8 carried MtPHY1 under the control of the MtPT1 promoter, line 11 carried MtPHY1 under the control of CaMV35S promoter.

EXAMPLE 4

Phytase Activity and Secretion in Transgenic Plants

To assess phytase activities in root extracts of the three transgenic lines (2, 8, 11), each were grown in agar medium containing phytate as the sole source of P. Measurement of phytase activity essentially followed the procedure described by Richardson et al., (2001). Samples of whole root tissues (four replicates, 30 plants per replicate) were ground in a mortar and pestle with three volumes (v/w) of MES/Ca buffer (15 mM MES buffer with 0.5 mM $CaCl_2$, pH 5.5) containing 1 mM EDTA. Extracts were then centrifuged for 10 min at 12,000 g; 250 µl of the crude extract was added to a total volume of 500 µl MES/Ca buffer containing 2 mM phytate. The reaction was incubated at 27° C. for 60 min and was terminated by the addition of an equal volume of 10% TCA. Phytase activity was calculated from the release of $P_i$ over the incubation period by spectrophotometry at 882 nm using the molybdate-blue procedure (Murphy and Riley 1962). The protein concentrations were determined using Bio-Rad Dc protein assay reagent (Bio-Rad Laboratories, Hercules, Calif.) with bovine serum albumin as standard. Enzyme activity was calculated as mU per mg protein, where 1 unit (U) releases 1 µmol Pi $min^{-1}$ under the assay conditions described (Richardson et al., 2001). Phytase activities in whole root extracts of the transgenic lines were found to only be 22% to 36% higher than that of the control plants (FIG. 4*a*).

For the measurement of phytase activity in root apoplast, 5 µl of apoplast sap obtained from roots by the centrifugation method (Yu et al., 1999) was added to a total volume of 100 µl of MES/Ca buffer containing 2 mM phytate. The reaction conditions and the calculations of the enzyme activity were the same as the procedure used for whole root extract as described above. In contrast to the results obtained with whole root extracts, phytase activities in apoplast of transgenic plant roots were 12.3- to 16.2-fold of that in the empty vector control plants (FIG. 4*b*). The results further confirmed that much of the phytase produced was secreted into apoplast. Phytase activity of transgenic line 8 (MtPT1::MtPHY1) was significantly higher than that of transgenic line 11, which carried MtPHY1 under the control of CaMV35S promoter. Phytase activity of another MtPT1 promoter driven MtPHY1 line, line 2, was similar to the CaMV35S driven MtPHY1 line.

To further characterize the activity of phytase in the transgenic plant seeds of the transgenic lines as well as the empty vector control line were sown on normal MS agar medium. Fifteen-day-old seedlings were carefully transferred to 50 ml plastic tubes containing 20 ml liquid modified MS medium in which Pi was replaced by phytate. The tubes were fixed in a rack and the seedlings were grown for seven more days in a shaker at 40 rpm. The roots were then harvested, washed with deionized water and incubated in 50 ml of 5 mM maleate buffer, pH 5.5, containing 2 mM $CaCl_2$, 0.01% protease inhibitor cocktail (Sigma, St. Louis, Mo.) and 2 mM InsP6 (Sigma, St. Louis, Mo.). One milliliter was sampled at time points 0, 12 and 24 h and analyzed by HPLC, after the enzyme was inactivated by the addition of 0.5 ml 15% TCA. Myo-inositol 1,3,4,5,6-pentakisphosphate, myo-inositol 1,3,4,5-tetrakisphosphate, myo-inositol 1,4,5-triphosphate, myo-inositol 4,5-biphosphate and myo-inositol-4-monophosphate (all from Sigma, St. Louis, Mo.) were used as standard for InsP5, InsP4, InsP3, InsP2 and InsP1, respectively. The sum of InsP2, InsP1 and Ins was calculated as the difference between the total initial InsP6 and the sum of measured values for the other InsP forms (Zimmermann et al., 2003).

Results indicate that exudates from control roots degraded InsP6 at a low level (FIG. 5*a*), whereas root exudates from the transgenic lines degraded InsP6 rapidly with a concomitant accumulation of InsP5, InsP4, InsP3, InsP2, InsP1 and Ins (FIG. 5*b*). Most of the InsP6 was degraded after incubating transgenic plants for 24 h in liquid medium (FIG. 5*b*). Thus, the phytase secreted from the transgenic roots was able to degrade phytate in the liquid medium. Active phytase protein was visualized by staining for phosphomonoesterase activity. When plants were grown in agar with phytate as the sole source of P, roots of transgenic plants were stained darker than those of control plants (FIG. 6*a-c*), indicating the recombinant phytase was secreted into the rhizosphere directed by the native signal peptide.

EXAMPLE 5

The Effect of MtPHY1 Expression on Plant Growth, Biomass Production and Phosphate Uptake Ectopic expression of MtPHY1 in *Arabidopsis* did not result in phenotypic difference when plants were grown in agar medium with sufficient $P_i$ (2 mM). Dry matter weight, P concentration and total P content in the transgenics were similar to the control plants under $P_i$ sufficient conditions. However, large differences in plant growth, biomass production and P uptake were evident when the plants were supplied with phytate as the sole source of P (FIG. 6d).

Because of the P reserves, dry weight of 15-day-old (eight days on Pi sufficient agar medium, then seven days on phytate only medium) transgenic plants were only 14-20% higher than that of the control plants (FIG. 7a). The effects of transgene expression on the utilization of organic P became more evident following longer periods of growth on the phytate only medium. For 30-day-old plants, dry weight of the transgenic plants was 3.1- to 3.6-fold higher than the control plants (FIG. 7a). For 45-day-old plants, dry weight of the transgenic plants was 3.1- to 4.0-fold higher than the control plants (FIG. 7a). P concentrations of 30-day and 45-day plants increased 38.5-46.0% and 25.7-47.3%, respectively (FIG. 7b). Because of the drastic increase in total dry matter, total P contents in 30-day-old transgenic plants increased 4.1- to 4.9-fold, and total P contents in 45-day-old transgenic plants increased 4.1- to 5.5-fold (FIG. 7c).

EXAMPLE 6

Plant Growth of Transgenic White Clover Plants

White clover is an important forage legume. Transgenic white clover plants have been produced using the gene constructs MtPT1::MtPHY1 and CaMV35S::MtPHY1. When compared with control plants, better growth of the transgenic white clover plants was observed when phytate was used as the sole P source.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
Abdullah et al., *Biotechnology*, 4:1087, 1986.
Abelson, *Science*, 283:2015, 1999.
Altschul etal., *J. Mol. Biol.*, 215:403-410, 1990.
Bates, *Mol. Biotechnol.*, 2(2):135-145, 1994.
Battraw and Hall, *Theor. App. Genet.*, 82(2):161-168, 1991.
Bendtsen et al., *J. Mol. Biol.*, 340:783-795, 2004.
Bevan et al., *Nucleic Acids Research*, 11(2):369-385, 1983.
Bhattacharjee et al., *J. Plant Bioch. Biotech.* 6, (2):69-73. 1997.
Biocomputing: Informatics and Genome Projects, Smith (Ed.), Academic Press, NY, 1993.
Birren, et al., *Genome Analysis*, 1:543-559, 1997.
BLAST Manual, Altschul et al. (Eds.), NCBI NLM NIH, Bethesda, Md. 20894
Bower et al., *Plant J.*, 2:409-416. 1992.
Brinch-Pedersen et al., *Transgenic Res.*, 12:649-659, 2003.
Brinch-Pedersen et al., *Mol. Breed.*, 6:195-206, 2000.
Buising and Benbow, Mol Gen Genet, 243(1):71-81. 1994.
Callis et al., *Genes Dev.*, 1:1183-1200, 1987.
Carillo and Lipman, *SIAM J. Applied Math*, 48:1073, 1988.
Casa et al., *Proc. Natl. Acad. Sci. USA*, 90(23):11212-11216, 1993.
Chandler et al., *Plant Cell*, 1:1175-1183, 1989.
Chen et al., *Biotechniques*, 16:664-670, 1994.
Chiu et al., Curr. Biol., 6:325-330, 1996.
Chu et al., *Scientia Sinica*, 18:659-668, 1975.
Clough and Bent, *Plant J.*, 16:735-743, 1998.
Computational Molecular Biology, Lesk (Ed.), Oxford University Press, NY, 1988.
Computer Analysis of Sequence Data, Part I, Griffin and Griffin (Eds.), Humana Press, NJ, 1994.
Conkling etal., *Plant Physiol.*, 93:1203-1211, 1990.
Coulson, *Trends Biotech.*, 12:76-80, 1994.
DE 3642 829
De Block et al., *EMBO J.*, 6(9):2513-2518, 1987.
De Block et al., *Plant Physiol.*, 91:694-701, 1989.
Dellaporta et al., In: *Chromosome Structure and Function: Impact of New Concepts*, 18th Stadler Genetics Symposium, 11:263-282, 1988.
Devereux et al., *Nucleic Acids Res.*, 12(1):387, 1984.
Downward, *BMJ*, 328(7450):1245-1248, 2004.
Ebert et al., *Proc. Natl. Acad. Sci. USA*, 84:5745-5749, 1987.
Emanuelsson et al., *J. Mol. Biol.*, 300:1005-1016, 2000.
EPA App. 154,204
Fire et al., *Nature*, 391(6669):806-811, 1998.
Fraley et al., *Bio/Technology*, 3:629-635, 1985.
Fromm et al., *Nature*, 3 19:791-793, 1986.
Gallie et al., *Plant Cell*, 1:301-311, 1989.
Gaston et al., *J. Environ. Qual.*, 32:1422-1429, 2003.
Gelvin et al., In: *Plant Molecular Biology Manual*, 1990.
Ghosh-Biswas et al., *J. Biotechnol.*, 32(1):1-10, 1994.
Hagio et al., *Plant Cell Rep.*, 10(5):260-264, 1991.
Haseloffet et al., *Proc. Natl. Acad. Sci. USA*, 94(6):2122-2127, 1997.
Hayes et al., *J. Plant Physiol.*, 26:801-809, 1999.
Hayes et al., *Plant Soil*, 220:165-174, 2000.
He et al., *Plant Cell Reports*, 14(2-3):192-196, 1994.
Hegeman and Grabau, *Plant Physiol.*, 126:1598-1608, 2001.
Hensgens et al., *Plant Mol. Biol.*, 22(6):1101-1127, 1993.
Hentikoff and Hentikoff, *Proc. Natl. Acad. Sci USA*, 89:10915-10919, 1992.
Hiei et al., *Plant Mol. Biol.*, 35(1-2):205-218, 1997.
Hinchee et al., *BioTechnol.*, 6:915-922, 1988.
Hübel and Beck, *Plant Physiol.*, 112:1429-1436, 1996.
Hudspeth and Grula, *Plant Mol. Biol.*, 12:579-589, 1989.
Ikuta et al., *BioTechnol.*, 8:241-242, 1990.

Ishidia et al., *Nat. Biotechnol.*, 14(6):745-750, 1996.
Iyamuremye and Dick, *Advances in Agronomy*, 56:139-185, 1996.
Kaeppler et al., *Plant Cell Reports*, 9:415-418, 1990.
Kaeppler et al., *Theor. Appl. Genet.*, 84(5-6):560-566, 1992.
Katz et al., *J. Gen. Microbiol.*, 129:2703-2714, 1983.
Klee et al., *BioTechnology*, 3(7):637-642, 1985.
Knittel et al., *Plant Cell Reports*, 14(2-3):81-86, 1994.
Lawton et al., *Plant Mol. Biol.*, 9:315-324, 1987.
Lazzeri, *Methods Mol. Biol.*, 49:95-106, 1995.
Lehner et al., *Brief Funct. Genomic Proteomic.*, 3(1):68-83, 2004.
Li et al., *Plant Physiol.*, 114:1103-1111, 1997.
Liu et al., *Mol. Plant Microbe Interact.*, 11(1):14-22, 1998.
Maugenest et al., *Plant Mol. Biol.*, 39:503-514, 1999.
Maugenest et al., *Biochem. J.*, 322:511-517, 1997.
McCabe and Martinell, *BioTechnology*, 11(5):596-598, 1993.
McCormac et al., *Euphytica*, 99(1):17-25, 1998.
Mihaliak et al., *Meth. Plant Biochem.*, 9:261-279, 1993.
Mudge et al., *Plant Sci.*, 165:871-878, 2003.
Murakami et al., *Mol. Gen. Genet.*, 205:42-50, 1986.
Murashige and Skoog, *Physiol. Plant.*, 15:473-497, 1962.
Murashigeand Skoog, *Physiol. Plant.*, 15:473-497, 1962.
Murphy and Riley, *Anal. Chim. Acta*, 27:31-36, 1962.
Nagatani et al., *Biotech. Tech.*, 11(7):471-473, 1997.
Needleman and Wunsch, *J. Mol. Biol.*, 48:443-453, 1970.
Nielsen et al., *Protein Eng.*, 10:1-6, 1997.
Nielsen, *Nat. Biotechnol.*, 21(3):227-228, 2003.
Odell et al., *Nature*, 313:810-812, 1985.
Ogawa et al., *Sci. Rep.*, 13:42-48, 1973.
Olah and Sherwood, *Phytopathology*, 61:65-69, 1971.
Omirulleh et al., *Plant Mol. Biol.*, 21(3):415-428, 1993.
Ow et al., *Science*, 234:856-859, 1986.
PCT Appln. WO 92/17598
PCT Appln. WO 94/09699
PCT Appln. WO 95/06128
PCT Appln. WO 97/04103
PCT Appln. WO 97/41228
Pote et al., *J. Environ. Qual.*, 32:2392-2398, 2003.
Potrykus et al., *Mol. Gen. Genet.*, 199:183-188, 1985.
Prasher et al., *Biochem. Biophys. Res. Commun.*, 126(3): 1259-1268, 1985.
Raghothama, *Annu. Rev. Plant Physiol. Plant Mol. Biol.*, 50:665-693, 1999.
Reichel et al., *Proc. Natl. Acad. Sci. USA*, 93(12):5888-5893, 1996.
Richardson et al., *Plant Cell Environ.*, 23:397-405, 2000.
Richardson et al., *Plant J.*, 25:641-649, 2001.
Ritala et al., *Plant Mol. Biol.*, 24(2):317-325, 1994.
Roe and Kupfer, In Molecular Breeding of Forage and Turf, Hopkins et al., (Eds.), Kiuwer Academic Publishers, Dordrecht, 333-344, 2004.
Rogers et al., *Methods Enzymol.*, 153:253-277, 1987.
Rommens et al., *Plant Physiol.*, 135:421-431, 2004.
Sambrook et al., In: *Molecular cloning: a laboratory manual*, 2nd Ed., Cold Spring Harbor Laboratory, NY, 1989.
Schumacher et al., *Plant Cell Rep.*, 6:410-413, 1987.
Sequence Analysis in Molecular Biology, von Heinje (Ed.), Academic Press, NY, 1987.
Sequence Analysis Primer, Gribskov and Devereux (Eds.), Stockton Press, NY, 1991.
Sheen et al., *Plant J.*, 8(5):777-784, 1995.
Singsit et al., *Transgenic Res.*, 6(2):169-176, 1997.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Thomas et al., *Plant Sci.* 69:189-198, 1990.
Thompson et al., *EMBO J.*, 6(9):2519-2523, 1987.
Thompson et al., *Euphytica*, 85(1-3):75-80, 1995.
Tian et al., *Plant Cell Rep.*, 16:267-271, 1997.
Tingay et al., *Plant J.*, 11(6):1369-1376, 1997.
Tomes et al., *Plant. Mol. Biol.* 14(2):261-268, 1990.
Torbet et al., *Crop Science*, 38(1):226-231, 1998.
Torbet et al., *Plant Cell Reports*, 14(10):635-640, 1995.
Toriyama et al., *Theor Appl. Genet.*, 73:16, 1986.
Tsukada et al., *Plant Cell Physiol.*, 30(4)599-604, 1989.
Twell et al., *Plant Physiol.*, 91:1270-1274, 1989.
Van Eck et al., *Plant Cell Reports*, 14(5):299-304, 1995.
Vance et al., *New Phytol.*, 157:423-447, 2003.
Vasil et al., *Plant Physiol.*, 91:1575-1579, 1989.
Vogel et al., *Arch. Biochem. Biophys.*, 401:164-172, 2002.
Volira and Satyanarayana, *Crit. Rev. Biotechnol.*, 23:29-60, 2003.
Von Uexküll and Mutert, *Plant Soil*, 171:1-15, 1995.
Walker et al., *Proc. Natl. Acad. Sci. USA*, 84:6624-6628, 1987.
Wang et al., *Molec. Cell. Biol.*, 12(8):3399-3406, 1992.
Whitelaw, *Advances in Agronomy*, 69:99-151, 2000.
Wodzinski and Ullah, *Adv. Appl. Microbiol.*, 42:263-302, 1996.
Yamada et al., *Plant Cell Rep.*, 4:85, 1986.
Yang and Russell, *Proc. Natl. Acad. Sci. USA*, 87:4144-4148, 1990.
Yu et al. *New Phytol.*, 143:299-304, 1999.
Zheng and Edwards, *J. Gen. Virol.*, 71:1865-1868, 1990.
Zimmermann et al. *Plant Biotechnol. J.*, 1:353-360, 2003.
Zukowsky et al., *Proc. Natl. Acad. Sci. USA*, 80:1101-1105, 1983.

What is claimed is:

1. An isolated nucleic acid sequence, wherein the nucleic acid sequence is selected from the group consisting of: (a) a nucleic acid sequence encoding the polypeptide of SEQ ID NO:2; (b) a nucleic acid sequence comprising the sequence of SEQ ID NO:1; (c) a nucleic acid sequence hybridizing to SEQ ID NO:1 under wash conditions of 0.15 M NaCl and 70° C. for 10 minutes, wherein the sequence encodes phytase; (d) a nucleic acid sequence comprising at least 90% sequence identity over the full length of the nucleic acid sequence of SEQ ID NO:1 wherein the sequence encodes phytase; and (e) a nucleic acid sequence fully complementary to the nucleic acid sequence of (a), (b), (c) or (d).

2. The isolated nucleic acid sequence of claim 1, further defined as operably linked to a heterologous promoter functional in plants.

3. A recombinant vector comprising the isolated nucleic acid sequence of claim 1 operably linked to a heterologous promoter.

4. The recombinant vector of claim 3, further comprising at least one additional sequence chosen from the group consisting of: a regulatory sequence, a selectable marker, a leader sequence and a terminator.

5. The recombinant vector of claim 4, wherein the additional sequence is a heterologous sequence.

6. The recombinant vector of claim 3, wherein the promoter is a tissue-specific promoter.

7. The recombinant vector of claim 3, wherein the promoter is a root-specific promoter.

8. The recombinant vector of claim 3, defined as an isolated expression cassette.

9. A transgenic plant transformed with the recombinant vector of claim 3.

10. The transgenic plant of claim 9, further defined as a monocotyledonous plant.

11. The transgenic plant of claim 9, further defined as a dicotyledonous plant.

12. The transgenic plant of claim 9, further defined as a legume.

13. The transgenic plant of claim 9, further defined as an $R_0$ transgenic plant.

14. The transgenic plant of claim 9, further defined as a progeny plant of any generation of an $R_0$ transgenic plant, wherein the transgenic plant has the recombinant vector from the $R_0$ transgenic plant.

15. A seed of the transgenic plant of claim 9, wherein the seed comprises the recombinant vector.

16. A host cell transformed with the recombinant vector of claim 3.

17. The host cell of claim 16, wherein said host cell is a plant cell.

18. A method of increasing phosphorous utilization in a plant comprising introducing into the plant the recombinant vector according to claim 3, wherein the nucleic acid sequence is expressed and wherein the plant exhibits increased phosphorous uptake relative to a plant of the same genotype lacking the nucleic acid sequence.

19. The method of claim 18, wherein the recombinant vector is inherited from a parent plant of said plant.

20. The method of claim 18, wherein the plant is directly transformed with the recombinant vector.

21. The isolated nucleic acid sequence of claim 1, wherein the nucleic acid sequence is a nucleic acid sequence comprising at least 95% sequence identity over the full length of the nucleic acid sequence of SEQ ID NO:1 wherein the sequence encodes phytase.

22. The isolated nucleic acid sequence of claim 1, wherein the nucleic acid sequence is a nucleic acid sequence comprising at least 98% sequence identity over the full length of the nucleic acid sequence of SEQ ID NO:1 wherein the sequence encodes phytase.

* * * * *